US 6,313,464 B1

(12) United States Patent
Schrader

(10) Patent No.: US 6,313,464 B1
(45) Date of Patent: Nov. 6, 2001

(54) INFRARED, MULTIPLE GAS ANALYZER AND METHODS FOR GAS ANALYSIS

(76) Inventor: Robert J. Schrader, 1801 Clement Ave., Suite 200, Alameda, CA (US) 94501

( * ) Notice: Subject to any disclaimer, the term of this patent is extended or adjusted under 35 U.S.C. 154(b) by 0 days.

(21) Appl. No.: 09/639,553

(22) Filed: Aug. 16, 2000

Related U.S. Application Data

(62) Division of application No. 09/099,141, filed on Jun. 18, 1998, now Pat. No. 6,201,245.

(51) Int. Cl.⁷ .................................................. G01J 5/08
(52) U.S. Cl. ............................................. 250/349; 250/343
(58) Field of Search ................................. 250/343, 345, 250/344

(56) References Cited

U.S. PATENT DOCUMENTS

| | | | | |
|---|---|---|---|---|
| 3,797,942 | * | 3/1974 | Joly | 356/410 |
| 4,228,352 | * | 10/1980 | Adrian | 250/343 |
| 4,914,719 | * | 4/1990 | Conlon et al. | 250/339.13 |
| 5,163,332 | * | 11/1992 | Wong | 73/863.23 |
| 5,222,389 | * | 6/1993 | Wong | 73/31.02 |
| 5,689,114 | * | 11/1997 | Miyazaki et al. | 250/343 |

* cited by examiner

Primary Examiner—Constantine Hannaher
Assistant Examiner—Albert Gagliardi
(74) Attorney, Agent, or Firm—Edward J. Da Rin, Esq.

(57) ABSTRACT

A portable, infrared, multiple gas analyzer for measuring the concentration of a plurality of infrared absorbent gases with a simple optical arrangement for transmitting an infrared beam along an optical path along with gas mixtures to be analyzed. Light transmitting tubes arranged in a U-like configuration transmit infrared energy and the gases applied thereto over a small path to an infrared detector from an infrared source and provide electrical analog output signals representative of the detected gases. The detector output signals are processed by D.C. processing circuits including an analog to digital converter and microprocessing circuits for providing digital, binary coded, output signals representative of the detected gas concentration of the infrared absorbent gases. The analyzer can be readily calibrated by applying a non-infrared absorbent gas to the gas analyzer to provide a maximum output signal level with the infrared beam on and the background level or dark level signal with the beam off. The gas mixture having the infrared absorbent gases to be measured are applied to the analyzer for measurement and the resulting analog signals are amplified under control of a microprocessor for determining whether or not a preselected signal level stored in the microprocessor memory is exceeded or not. If not, the gain of the amplifier is increased to compensate for the aging of the analyzer. An offset voltage is applied to the analog to digital converter under control of the microprocessor to the amplified gas signals for increasing the resolution of the converter output signals only during the time intervals the absorbent gases are being measured. The microprocessor is programmed to execute a program for calculating the detected concentration of the gases undergoing analysis based on the previously acquired and stored "zero" gas level, dark level and known gas factors to provide the desired digital, binary coded, gas concentration signal from the analyzer.

10 Claims, 7 Drawing Sheets

INFRARED, MULTIPLE GAS ANALYZER AND METHODS FOR GAS ANALYSIS

This application is a division of application Ser. No. 09/099,141, filed on Jun. 18 1998; and now is U.S. Pat. No. 6,201,245, granted on Mar. 21, 2001.

BACKGROUND OF THE INVENTION

This invention relates to a portable, infrared gas analyzer capable of measuring multiple gases in a gas sample having one or more infrared absorption gases therein for signalling the concentration of the selected gas or gases in the gas mixture, such as the exhaust gases of gasoline powered engines without resorting to the use of chopping techniques.

Infrared gas analyzers utilizing the infrared absorption principle for determining the quantity of two or more gases in a sample gas to be measured are well known in the art. The infrared absorption principle is based on the fact that the photons are absorbed by an infrared sensitive gas in proportion to the concentration of the gas. The typical prior art infrared gas analyzer relies on the use of a chopper for repeatively and continuously interrupting the infrared beam at a predetermined rate. This prior art technique is resorted to measure the "dark level" or background signal that is present when no infrared beam is applied to the analyzer. Typical prior art patent disclosing these infrared gas analyzers are disclosed in U.S. Pat. Nos. 3,932,754; 4,069,420; 4,420,687, and 4,772,790. Typically these prior art devices employ multiple thermopiles for detecting and signalling the infrared level of the infrared beam applied to the analyzer.

Most of the known prior art infrared analyzers utilized collimated or focused infrared beams in the optical portion and do not permit the infrared beam to reflect off anything but mirrors and as a result require expensive optical systems to control the infrared beams. These prior art systems require splitting the infrared beam by a physical beam splitter or a dichroic beam splitter and the like that must be properly mounted and aligned and produces optical losses due to the beam splitting designs. In addition, these devices require relatively long optical path lengths that may vary from 1-meter to more than 100-meters.

SUMMARY OF THE INVENTION

The present invention comprehends a multiple gas infrared beam analyzers that is portable, compact, and operable with a low power battery pack that is easy to integrate into Host Instruments. The multiple gas analyzer is cost effective and an efficient design that does not incorporate the aforementioned costly features for implementing the aforementioned prior art methods for infrared gas analyzers and measures multiple infrared sensitive gases present in the exhaust gases of a gas powered engine such as carbon monixide, CO, or hydrocarbons, propane or hexane. The hydrocarbons are measured by measuring the hydrocarbon molecular bonds and therefore respond to any gaseous compound containing hydrocarbon bonds in it but the analyzer of the invention is calibrated for carbon monoxide, propane, and hexane. This is intended to measure the unburned hydrocarbons in gasoline but is useful for measuring propane, butane and natural gas fueled combustion engines. The hexane is measured since it is the hydrocarbon which most closely represents gasoline vapor and is an international standard for the gasoline fueled engines. The multiple gas analyzer utilizes thermopile detectors, in a non-chopped configuration to detect decreases in the infrared radiation that are monotonically related to the concentration of the measured gas or gases in the gas mixture applied to the infrared analzer. The infrared optical system is simple, optically efficient and arranged in a unique configuration. The overall path length for the gases to be measured is less than 5-inches. The optical system is operative with non-collimated infrared source and having a folded beam arranged with minimal losses and a space saving arrangement.

From a structural standpoint, the present invention comprises a compact infrared optical system that reflects an infrared beam along internally reflecting, light transmitting pipes over a preselected light path and reflected from mirrors for folding or changing the direction of the infrared beam to confine it within relatively small path to impinge against a plurality of infrared detector-filters for detecting a plurality of gases. The infrared detector-filters are each designed to respond to an individual gas and provide an electrical output signal representative of the concentration of the detected gas in the gas mixture. The detector-filters are advantageously arranged within the infrared analyzer to take advantage of the reflective properties of the detector-filter to cause the reflected beam from one of the detector-filters to be reflected to another detector-filter for responding to a second gas in the gas mixture to provide an electrical output signal representative of the concentration of the second gas of the gas mixture all within a portable, relatively small infrared analyzer.

The infrared analyzer output signals are processed under the control of an analog to digital converter and a microcontroller programmed therefore and provide digital output signals representative of the multiple gas concentrations for transfer to a host processor. The electrical output signals from the infrared detectors are electronically processed including a variable gain amplifier, controlled by a microprocessor command to increase the amplifier gain upon determining that the analyzer has aged and/or been contaminated to provide amplified signals that compensate for the aging. The noise present in the amplified signal is filtered out to provide an analog signal containing the desired gas data, essentially noise free. This analog signal is applied to an analog to digital converter through a run-time offset voltage circuit to improve the resolution of the converter and provide more accurate binary, coded, digital output signals. The digital output signals are processed by a suitably programmed microprocessor for controlling the gain of the amplifier, the application of the offset voltage to the A/D converter during the gas measuring mode only and controls the energization of the infrared source during the calibration of the analyzer for providing the IR dark level value, the zero gas level and the continuous beam measurement mode.

BRIEF DESCRIPTION OF THE SEVERAL VIEWS OF THE DRAWINGS

These and other features of the present invention may be more fully appreciated when considered in the light of the following specifications and drawings, in which.

DETAILED DESCRIPTION OF THE INVENTION

Figure 1:
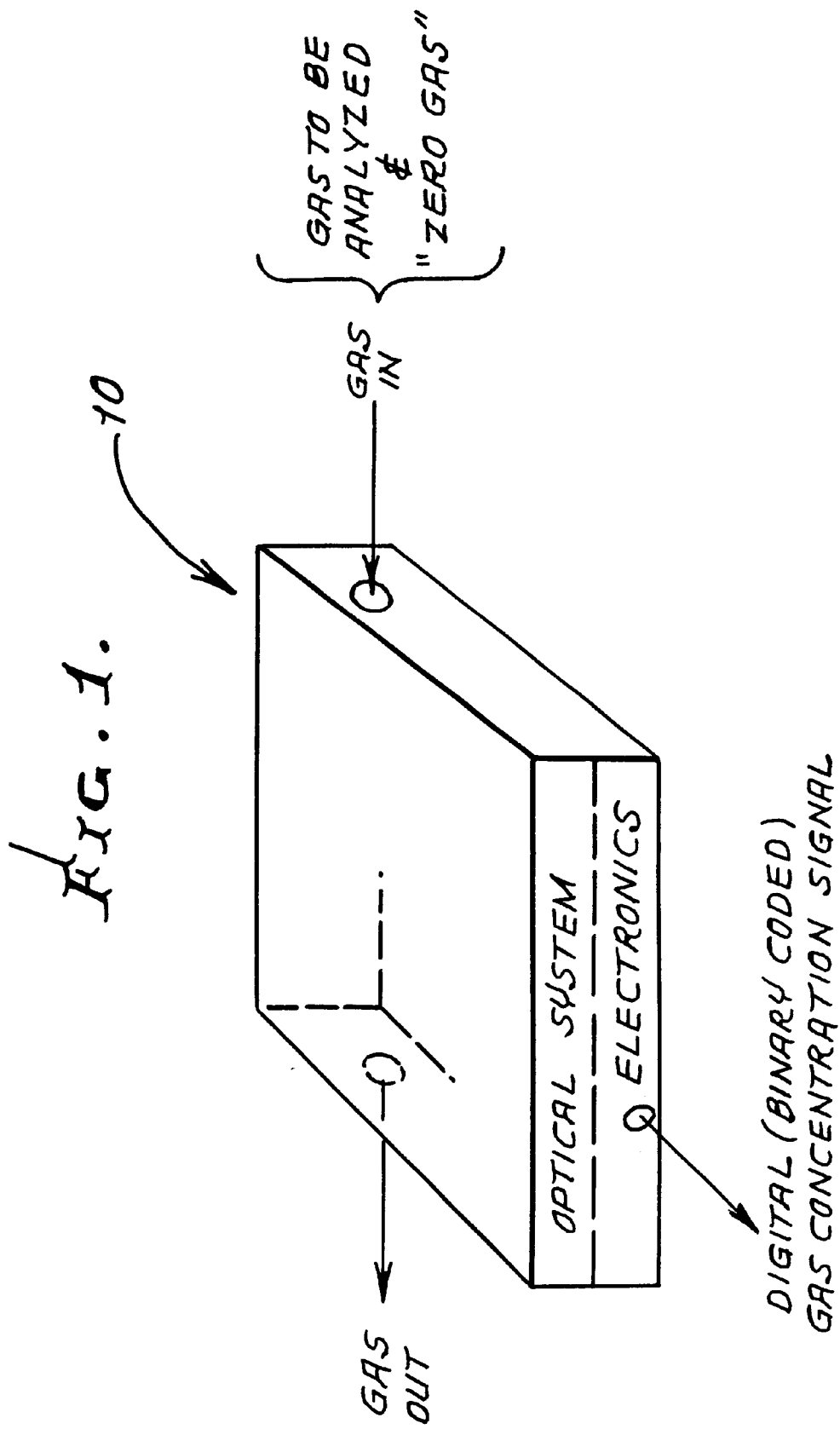
FIG. 1 is a diagrammatic view of the infrared gas analyzer embodying the present invention.

Now referring to the drawings, the gas analyzer in accordance with the present invention will be described. Referring to FIG. 1, a diagrammatic representation of the gas analyzer 10 is illustrated in its simple compact form. The gas analyzer 10 in its present final form is a compact module housing the gas sample cell and the associated electronics and microprocessor controls in a module on the order of two inches by two inches and one-half inches and one and one-half inches high and is operable with a battery pack. The electrical output signals from the digital, binary coded, signals representative of the detected gas concentration of the infrared absorbent gas coupled to the gas sample cell and subjected to a continuous infrared light beam. The analyzer 10 further houses an infrared detector for providing an electrical analog signal that is representative of the concentration of the gas to be analyzed and processed to provide the digital output signal.

Figure 2:
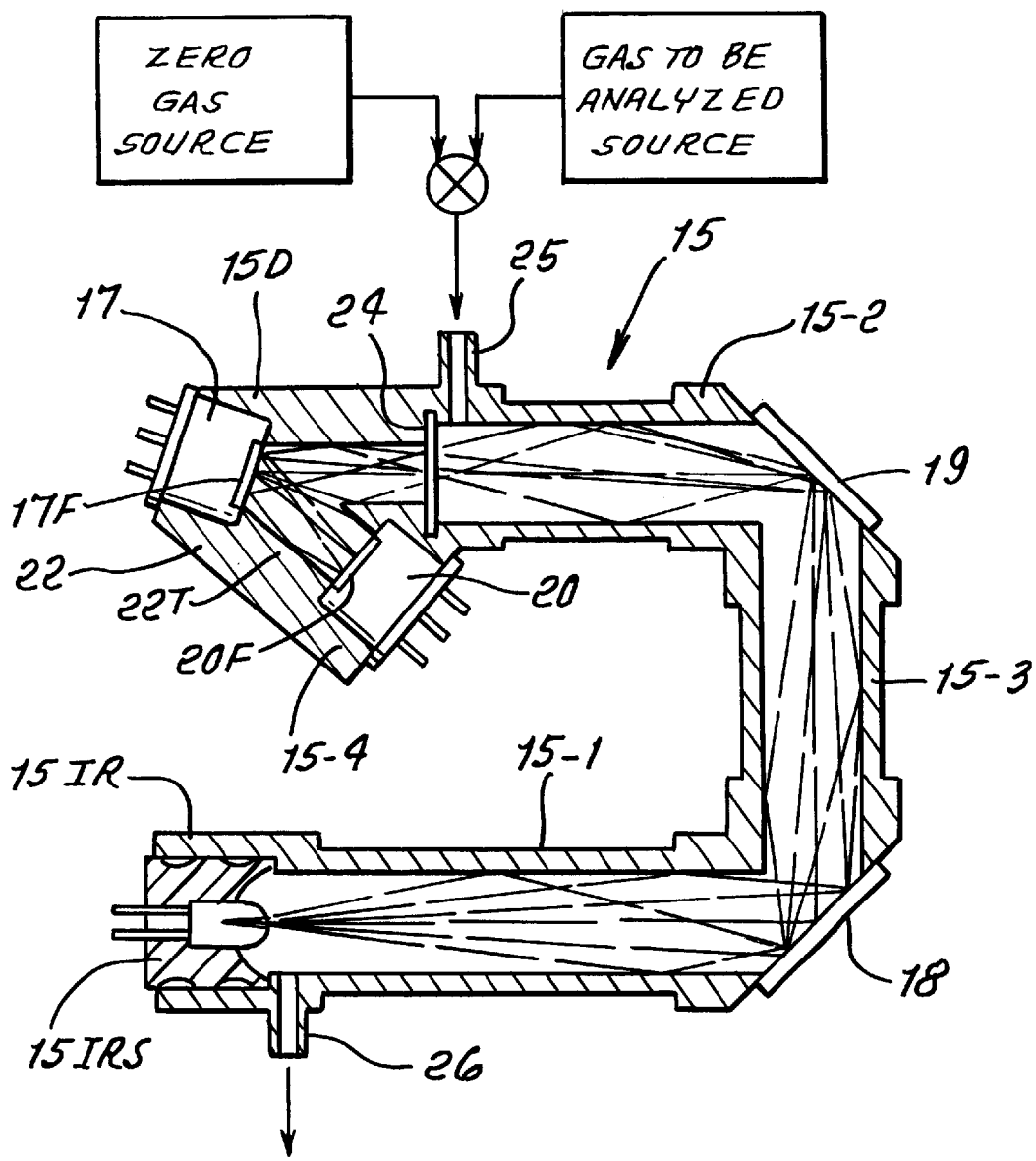
FIG. 2 is a diagrammatic top view of the infrared optical system for detecting multiple, infrared absorbing gases embodying the present invention.

The infrared optical system for the gas analyzer 10 is illustrated in FIG. 2 that defines the optical path of the infrared rays and the gas paths in terms of a U-like tubular structure 15. One end of one of the arms of the U-like structure 15, the end 15IR mounts a commercially available infrared source 15IRS that projects the infrared beam along the coupled, tubular light transmitting portion 15-1. The end of the other arm of the U-like structure 15, or the end 15D, mounts a commercially available infrared detector 17 that includes a thermopile array for detecting and signaling the infrared concentration of the infrared responsive gas undergoing analysis. As is presently conventional with the infrared detectors of the type of detector 17 they include a narrow-band pass infrared filter 17F for transmitting the band pass that includes the gas to be analyzed and reflects the remaining portion of the infrared light energy impinging on the filter 17F. The manner in which the detector 17 is oriented relative to the path of the infrared energy traveling in the U-like structure and its relationship with a second detector for providing a multiple gas analyzer will be described more fully hereinafter.

The U-like structure 15 comprises a plurality of light transmitting pipes in the illustrated U-like configuration. Each light transmitting pipe is provided with smooth, highly reflective inner walls for transmitting the infrared beam rays along the length of the light pipes. The light pipe 15-1 is mounted with the infrared source to directly receive the infrared beam therein and transmitted by means of internal reflections, as illustrated. The light pipe 15-1 forms one of the vertical arms of the U-like structure, while the other vertical arm is defined by the light pipe 15-2. The horizontal arm of the structure 15 comprises the horizontal light pipe 15-3. As illustrated, the adjacent light pipes 15-1 and 15-3 and the adjacent ends of the light pipes 15-2 and 15-3 are open ended. Each of these open ends are closed by a reflective mirror bridging the gaps between the light pipes.

The front, reflective surface of the mirrors 18 and 19 are mounted to reflect the light rays within the light pipes. The mirror 18 bridges the gap between the light pipes 15-1 and 15-3 while the mirror 19 bridges the gap between the light pipes 15-2 and 15-3, as is clearly evident from examining FIG. 2. With this U-like structure the infrared beam provided by the source 15IRS is confined within the light pipe 15-1, 15-2 and 15-3 except when they are reflected by the mirrors 18 and 19 into the adjacent light pipes 15-3 and 15-2. The mirrors 18 and 19 are mounted at approximately 45 degrees to the axis of the transmitting light pipe so to reflect the non-collimated beam at an angle of 90 degrees from incidence angle of the light ray. This permits a 5 inch gas sample path to be folded or fit a 2.5 inch space with a minimal loss of light energy and lends itself to ease in packaging and easier to maintain a uniform temperature so as to provide superior performance. This optical arrangement itself is considered to be a unique feature of the invention.

As noted hereinabove, the infrared detector 17 is mounted to receive the light rays transmitted along the light pipe 15-2. The manner in which the infrared detectors are mounted in the optical path in accordance with the present invention is unique in permitting multiple gases to be detected in utilizing the U-like structure. Although, it is conventional to have a reflective filter at the entry of the infrared detector, it has not been utilized to transmit the reflective light energy to another detector-filter to permit multiple gases to be analyzed. This technique permits beam splitting without resorting to expensive physical beam splitters or dichroic beam splitters. The advantage of utilizing the reflective energy for the second detector is that precise beam splitting occurs without extra precision, expensive optical elements that require precise mounting, aligning without the accompanying optical losses. For this purpose, the detector 17 is mounted at an acute angle to receive the light energy transmitted through the light pipe 15-2 and reflected down an additional light pipe 15-4 arranged at an angle of approximately twice the angle of the acute angle for the detector 17 for the transmitting the reflected light from the filter 17-F to a second infrared detector 20 having an entry infrared narrow band filter 20F for transmitting the desired band pass including that for a second gas to be analyzed. The U-like structure 15, for the purpose of mounting the second detector 20 for integrating it into the structure 15 utilizes an additional arm 22 extending from the end 15D of the structure 15 inwardly of the U-like structure at said preselected angle mentioned hereinabove. The arm 22 mounts a light transmitting pipe 22T defined by the internal walls of the arm 22, as illustrated and sized relative to the input apertures of the detectors 17 and 20 to transmit the reflected light energy from the filter 17F to the filter 20F and in turn to the detector 20. For accomodating the input aperture of the filter 17F, the light pipe 15 is reduced in internal diameter for transmitting the light rays to the detector 17 as illustrated.

A light transparent, gas seal 24 is secured to the shoulder of the light pipe defined by the reduced internal diameter as illustrated in FIG. 2. The gas seal 24 prevents the gases from being transmitted while transmitting the light energy to the detector 17. This same arrangement can be used to utilize the reflected energy from the filter 20F to a third detector or a fourth detector for analyzing multiple gases in a gas mixture applied to the analyzer. This optical system configuration provides the most simple and optically efficient design that can be expanded to incorporate additional detectors, all operating at their own unique wavelengths derived from a single infrared beam. For example, the gases that may be analyzed may be a hydrocarbon, carbon monoxide, carbon dioxide and a reference detector. The structure 15 is provided with a gas inlet port 25 extending through the wall of the light pipe 15-2 adjacent the gas seal 24. A gas outlet port 26 is defined in the wall of the light pipe 15-1 adjacent exit end of the infrared source 15IRS. In this manner the gases being analyzed flow from the detector 17 housing to the infrared source housing 15IRS. In the practical application of the analyzer 10, the detector 17 and the associated filter 17F are designed to detect carbon monoxide in a gas mixture applied to the analyzer. Similarly, the detector 20 and the associated filter 20F are designed to measure either of the hydrocarbons, propane or hexane. Specifically, the exhaust gases of a gasoline may be analyzed for these gases by means of the analyzer 10.

Figure 3:
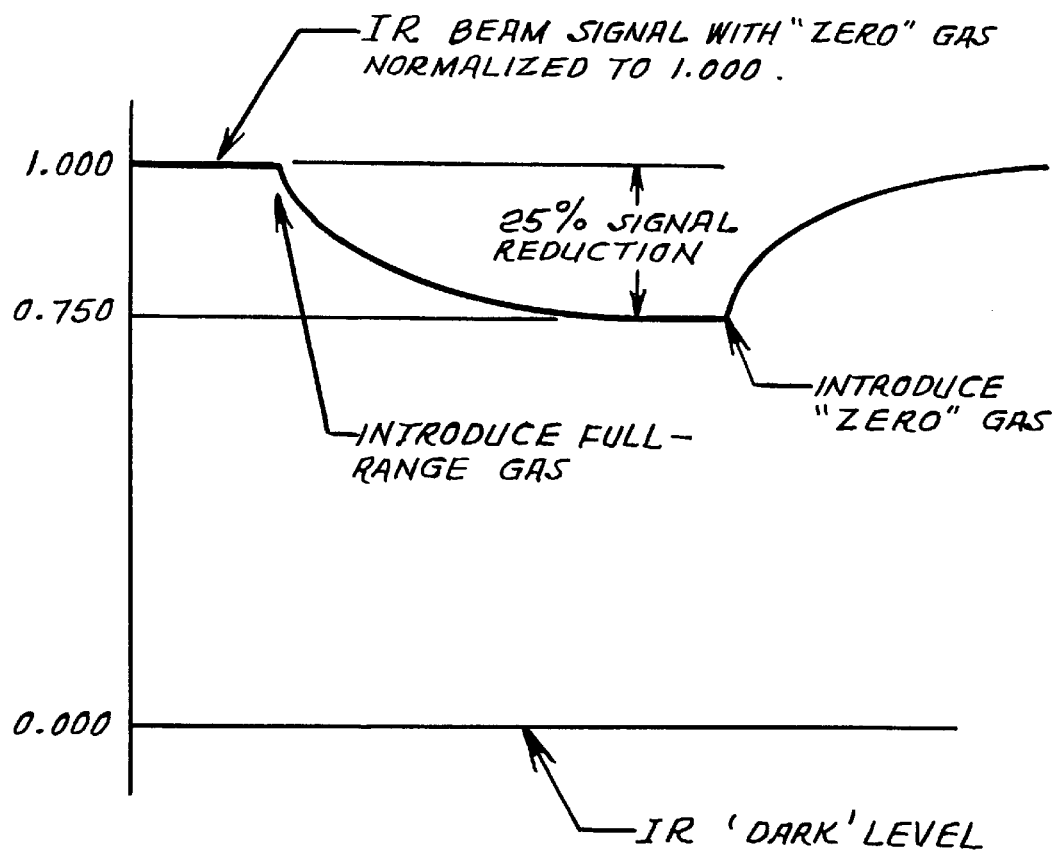
FIG. 3 is a diagrammatic representation of the typical infrared signal levels of the various signals for calibrating the analyzer and measuring the desired gases for acquiring the gas concentration signals.

Unlike the prior art analyzers, the present invention does not utilize conventional chopping or equivalent techniques but utilizes a continuous infrared beam and operating the electronic processing circuits in the D.C. mode while separating the infrared beam gas measurements and dark level correction functions. To appreciate and fully understand the merits of the present unique mode of operation it is important to understand the various electrical signals and the analysis process of the infrared gas analysis as represented FIG. 3. In the prior art, infrared gas analysis is accomplished by measuring the change in the infrared signal level as it travels in gas sample cell. In the present invention when no infrared absorbing gas or "zero" gas is applied the sample cell, the maximum light energy is present throughout and the detector output signal is at a maximum value. This condition is illustrated in FIG. 3 as the "zero" gas condition and is illustrated as normalized at 1,000. When a full range gas mixture including infrared absorbing gases are applied to the analyzer 10, the infrared beam is reduced in amplitude by an amount related to the concentration of the gas being analyzed. The relationship between the infrared signal absorption and gas concentration is highly non-linear as the signal absorption increases. The signal absorption illustrated in FIG. 3 is a 25% reduction in the amplitude of the signal during the gas measurement period. This results in a continuous DC signal that changes over seconds. When no gas is applied to the analyzer and the infrared source is turned off, the output signal provided by the detector is identified as the IR 'dark' level and is always present in the analyzer 10. The IR dark level in FIG. 3 is referenced to 0.000—not to a zero voltage level. The output signals from the detector representative of the gas information content contain the gas information and the dark level information. The gas information signal should be referenced to the IR dark level and the analyzer should correct the gas information signal to compensate for any changes in the IR dark level signal during analysis. Because the infrared gas information signal is continuous and varies over seconds (see FIG. 3) the signal contains the highest gas information content available about the light energy in the infrared beam which can not be achieved by known prior art structures. Simple high-frequency noise filtering is all that is required in the present invention to produce a very noise-free signal relating to the infrared gas information signal. This result is produced by the present invention by always operating the analyzer in a D.C. mode, and separating the IR beam gas measurement intervals from the dark level correction functions. As noted in FIG. 3, at the completion of the gas measurement interval, the "zero" gas is applied to the analyzer and the output signal slowly increases to its maximum level.

It should be noted that the automatic controls for sequentially applying a gas mixture to be measured and the "zero" gas as indicated in FIG. 1 for the purposes of the present invention is outside the scope of the present disclosure and is considered to be within the skill of the art to accomplish. The gas analyzer 10 can be calibrated to acquire and store in a computer memory the IR dark level and the zero gas level for use in subsequent gas concentration calculations. The acquired values for the IR dark level and zero gas are updated every time the analyzer is zero calibrated as will be discussed more fully hereinafter. The dark level value can be updated at anytime, independent of the gas in the sample cell by turning the infrared source off, allow it to cool and then acquire the IR dark level.

Figure 4:
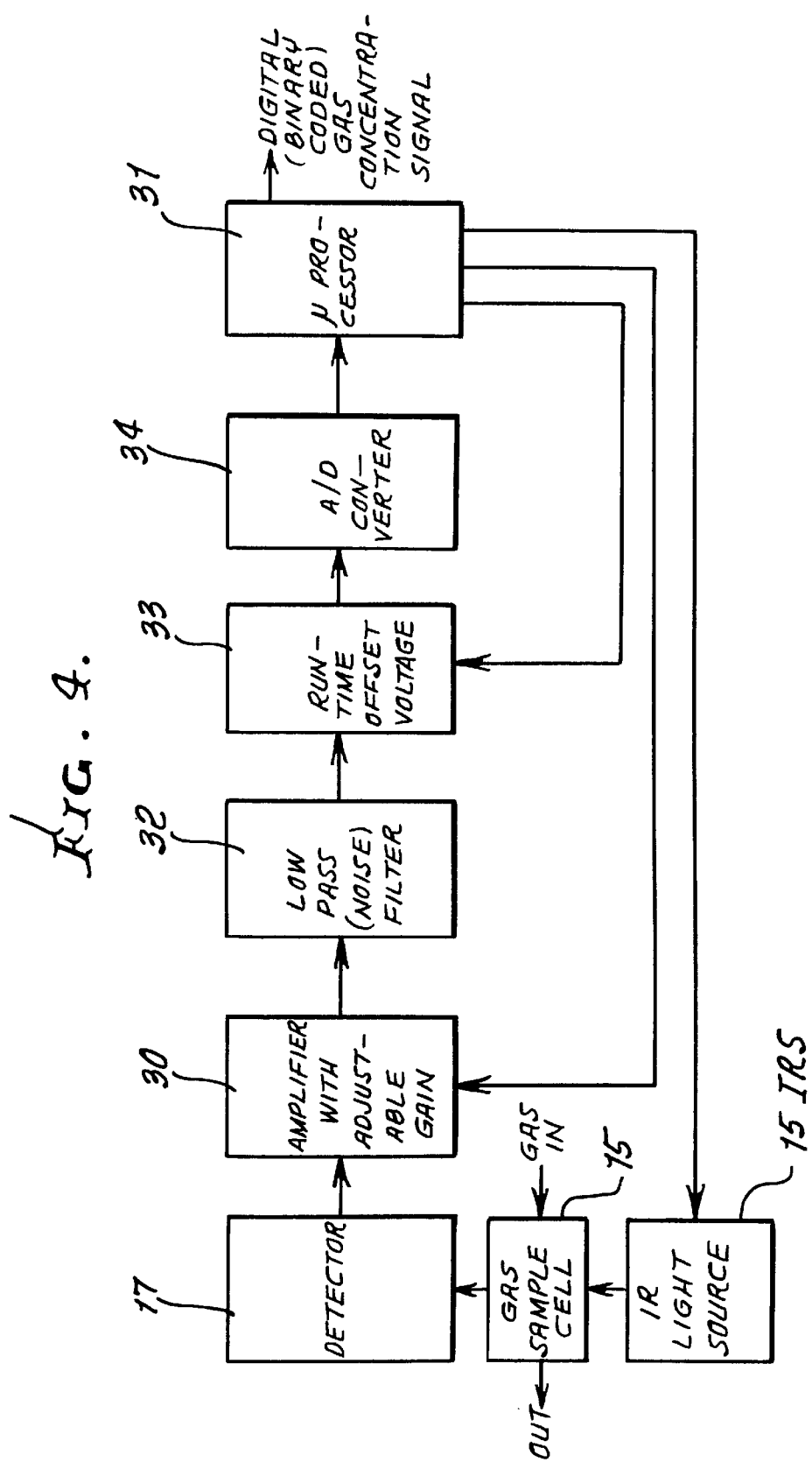
FIG. 4 is a block diagram of the electronic-microprocessor control circuits for the gas analyzer for measuring carbon monoxide and hydrocarbons.

With the above concepts in mind, the electronics for processing the output signals from the infrared detector will be described with reference to the block diagram of FIG. 4. The analyzer electronics of FIG. 4 is for a single channel or gas and for processing additional gases a second channel is necessary with the run-time offset output signal for the additional signal or signals being connected as a further input to the illustrated analog to digital, A/D, converter and controlled by the same microprocessor.

The analog signals provided by the detector 17 is coupled to an amplifier 30 with adjustable gain under control of a commercially available, programmable microprocessor 31. The low gain stage is the normal gain for the amplifier and is present when the system is new and the applied signals are at their maximum levels. As the system ages or is contaminated, the microprocessor determines at a preselected point to switch the amplifier to a high gain level to compensate for the degradation of the signal levels of the aged analyzer 10. The amplified signal is coupled to a low pass filter 32 to eliminate the noise portion of the amplified signal. The filtered signal is coupled to a run-time offset circuit 33 that is controlled from the microprocessor 31. The run-time offset voltage is a further feature possible by the continuous DC measurement technique so that the resolution of the analog to digital, A/D converter 34 can be significantly improved over prior art approaches by switching on the run-time offset under the command of the microprocessor 31 during the intervals of acquiring the gas data signal. By applying the run-time offset voltage to the converter 34, the full data acquisition of the converter can be applied to the continuous infrared beam signal while measuring the desired gas concentration. For example, if the converter has 4096 binary bits of resolution, it would yield an output binary coded digital signal on the order of 1 millivolt per bit resolution. This offset may increase the resolution of the converter 34 by a factor of four. This offset voltage is possible to use in the present invention since the infrared data or gas beam and the dark level acquisition are accomplished in separate modes. The offset voltage is not applied during the acquisition of the dark level of the analyzer and thereby the converter 34 is centered around the analog ground level resulting in 1 millivolts per bit resolution is applied to obtain the dark level. As noted in FIG. 3, the highest infrared beam signal are significantly offset from zero volts, while the IR dark level ranges around zero volts. It should now be evident that the incorporation of the run-time offset and the mode switching between the IR beam gas data acquisition and the IR dark level acquisition increases the resolution of the converter 34 because of the characteristics of the gas analyzer of the present invention. If required, the resolution of the A/D converter 34 can be improved during the dark level acquisition by increasing the gain of the amplifier 30 by a factor of four or to 0.25 millivolts per binary bit. It should be noted that the dark level value can be updated at any time, independent of the gas in the sample cell, by merely turning off the infrared light source 15IRS, allowing the source to cool and then acquiring this infrared background level. Alternatively, the IR dark level may be obtained during the periodic zero gas calibration.

The binary coded digital output signals converts the analog signals coupled thereto to static binary coded digital signals that are fetched by the microprocessor 31 and operated thereon in accordance with the computer program stored therein. The microprocessor 31 includes associated digital signal storage capabilities for storing and updating the required system parameters. The microprocessor 31 can be readily programmed by those skilled programmers for executing the autogain routine, zero routine and a normal gas analysis to obtain a digital signal from the microprocessor representative of the detected concentration of the gas or gases analyzed.

Figure 5:
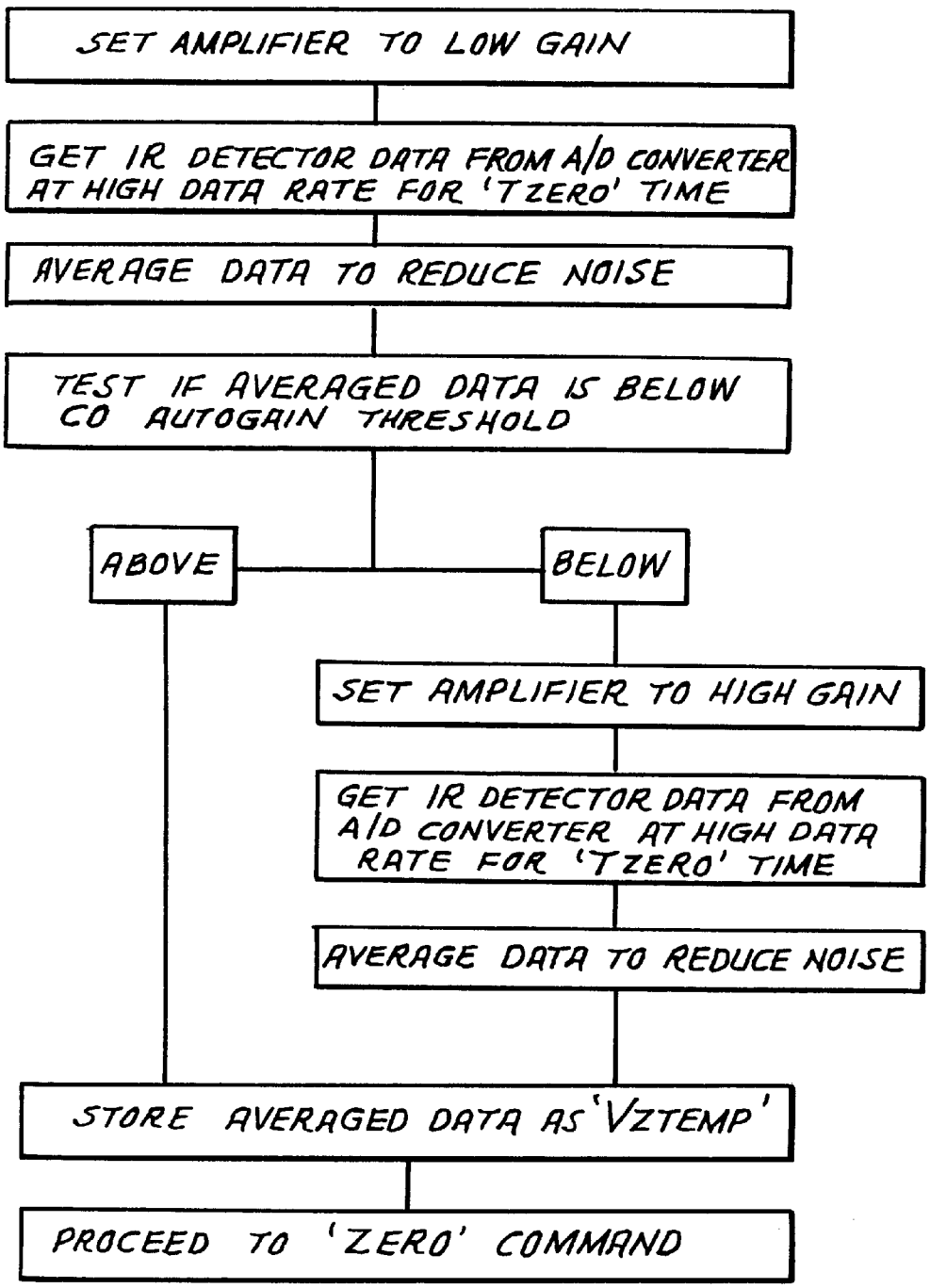
FIG. 5 is a functional flowchart of the autogain routine executed by the microprocessor for controlling the amplifier gain as illustrated in FIG. 4.
Figure 6:
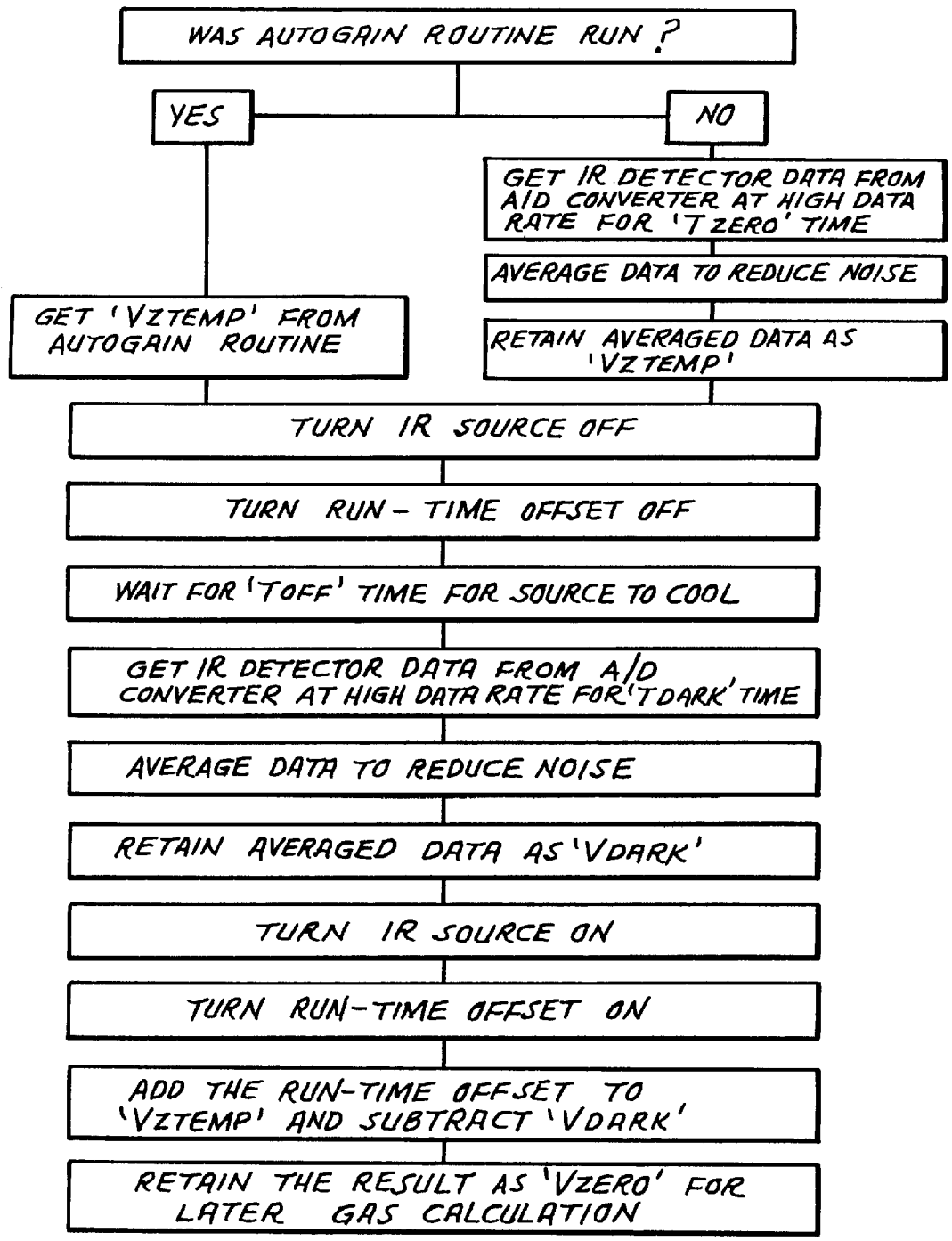
FIG. 6 is a functional flowchart of the zero routine executed by the microprocessor for measuring carbon monoxide and hydrocarbons.
Figure 7:
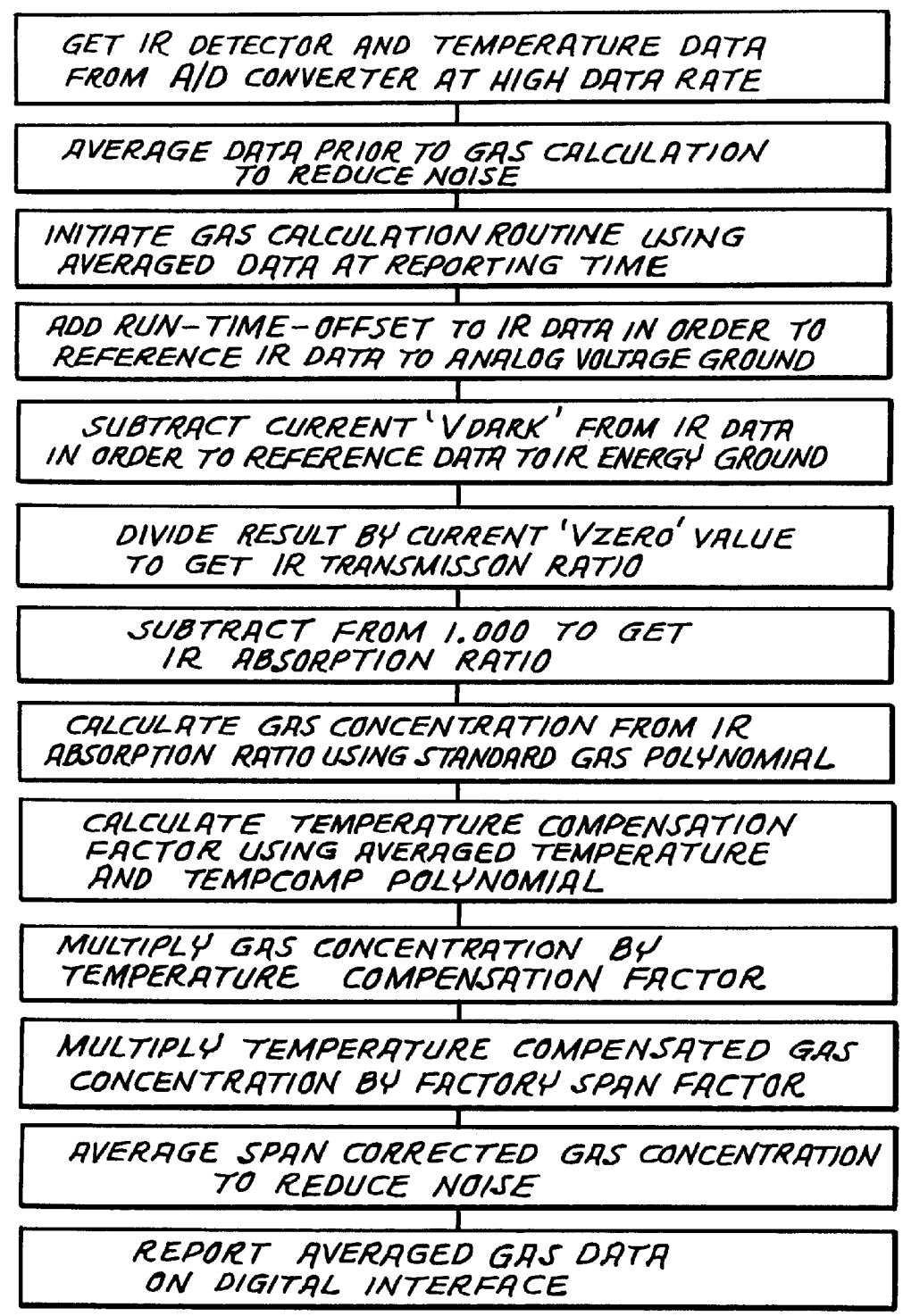
FIG. 7 is a functional flowchart of the normal gas analysis for the carbon monoxide and hydrocarbon channels and obtain binary coded, digital signals representative of the detected gas concentrations of the two gases.

The routines executed by the microprocessor 31 are illustrated in FIGS. 5–7 and will now be described. The flowchart of FIG. 5 illustrates the autogain routine functions for determining if the infrared beam signal has degraded as a result of aging and/or contamination of the optical system with usage of the analyzer 10. For this purpose the determination of whether or not the analyzer signals have degenerated is executed at the start of the zero gas routine as noted in FIGS. 5 and 6. During the autogain routine of the amplifier 30 is set to a low level of gain, the normal operating condition of the amplifier. For this purpose, it should be noted that a preselected threshold level is stored in the microprocessor memory for comparison with the electrical output signal produced with zero gas applied to the gas analyzer 10 with the amplifier 30 set in its low gain stage. Accordingly, during the time period a zero gas is applied to the gas analyzer 10, the output level of the signals provided by the detector 17 is compared by the microprocessor 31 to determine whether or not the detector signals are above or below the stored preselected threshold level. For this purpose the microprocessor 31 acquires the infrared detector output data from the A/D converter 34 at a high data rate for T zero time. The noise in the acquired signals are averaged out by the microprocessor 31 to reduce the noise level. The microprocessor 31 then compares this averaged data signals to determine if it is above or below the stored threshold level for the infrared absorbent gas to be analyzed shown as carbon monoxide in FIG. 5. If the zero signals are above the threshold level, the amplifier gain is maintained and the averaged data is stored in the computer memory as $V_{ztemp}$. As noted in FIG. 5, if the averaged data is found to be below the threshold level, the gain of amplifier 30 is set to a high gain level. The steps are then repeated with the amplifier 30 set in the high gain stage, to obtain the detector output data for T zero time. The noise in this data is reduced by averaging the data by the microprocessor and the data obtained with the amplifier 30 in the high gain level is stored in memory as the $V_{ztemp}$ signal.

The functional flowchart for the zero gas routine to be executed by the microprocessor 31 is illustrated in FIG. 6. Initially, as illustrated, a determination is made by the microprocessor whether or not the autogain routine of FIG. 5 has been executed, and if not it is then executed. If the microprocessor determines that the autogain routine has been executed, it fetches the $V_{ztemp}$ data from storage and turns the infrared source 15IRS off and then the run-time offset voltage is turned off. The infrared source is allowed to cool for a preselected time interval, identified as $T_{off}$ time. After the infrared beam source has cooled and the source is still off, the dark level output signal is acquired from the A/D converter at a high data rate for obtaining the dark level signal. This data is averaged out for noise reduction and then stored in the computer memory as the dark level signal $V_{dark}$. The next computer command turns on the infrared source 15IRS and then applies the run-time offset voltage to the amplified signals for application to the A/D converter. At this time the microprocessor adds the run-time offset voltage to $V_{ztemp}$ and substracts the dark-level signal, $V_{dark}$. The resulting value is stored in memory as $V_{zero}$ to be utilized in the later gas concentration calculation of FIG. 7.

The gas analysis process executed by the microprocessor 31 in terms of a functional flowchart in FIG. 7 utilizing the stored values of the zero gas level, the dark level and the acquired gas data signals for the single gas to be analyzed. At this point, it should be noted that the analog to digital converter 34 also provides a temperature data signal at its output provided by a temperature sensor arranged in the gas analyzer 10. This temperature sensor (not shown) produces a linear output voltage with temperature changes for making real time corrections for gas law effects. Accordingly, the microprocessor 31 initiates the gas analysis by fetching the gas data signals and temperature signals at a high data rate and then averaging the data for noise signal reduction prior to the gas concentration analysis. The gas calculation routine is started using averaged data at data reporting time for a preselected time interval. The run-time offset voltage is added to the gas data signal for referencing the infrared gas data to the analog voltage ground. The microprocessor 31, then obtains the current $V_{dark}$ signal and substracts it from the IR gas data signal in order to reference the gas data to IR energy ground level. It will be recalled, as noted hereinabove, the gas data signal derived from the infrared detector 17 comprises the gas data signal plus the infrared dark level.

The microprocessor 31 then acquires the current $V_{zero}$ value from storage and divides the result of the substraction process on the gas data signal by the acquired $V_{zero}$ value to obtain the infrared transmission ratio for the gas undergoing analysis. The computer next obtains the infrared absorption ratio by substracting 1.000 from the value of the IR transmission ratio. A standard, known gas polynomial had been previously stored in the computer memory for the individual gas being analyzed and is acquired by the microprocessor for calculating the gas concentration from the previously obtained IR absorption ratio and the standard gas polynomial. Similarly, a temperature compensation polynomial for the gas to be analyzed is placed in storage and is utilized by the microprocessor 31 for calculating a temperature compensation factor using the acquired, averaged temperature data. The next step executed is to multiply the previously calculated gas concentration data by the temperature compensation factor.

The computer memory further stores a factory span factor for the individual gas or gases undergoing analysis and is utilized by the microprocessor 31. The factory span factor is multiplied by the microprocessor by the temperature compensated gas. The result of the span corrected gas concentration is averaged to reduce the noise level of the signal and is emitted from the processor 31 of the analyzer 10. From the above description it should now be evident that with the successive and alternate application of the zero gas to the analyzer 10, that the necessary zero level, dark level and gas data signals are acquired and processed by the microprocessor along with the stored calculation factors to obtain a digital, binary coded, output signal representative of the gas concentration of the gas analyzed.

In the case of multiple gases that are analyzed, the same routines are executed by the microprocessor 31 to obtain the same signals for a second or third gas, such as a hydrocarbon and individually coupled to the input of the analog to digital converter 34. The autogain and zero routines are executed to determine if the amplifier of the second channel is to operate at a high or low level and the application of a run-time offset voltage to the second or hydrocarbon data prior to the application of the second gas data signal to the converter for increasing the accuracy of the converter as previously described for the first gas analyzed. Of course the standard calculation factors individual to the second or hydrocarbon are stored in memory for use in executing the gas analysis steps of FIG. 7.

In summary, then those skilled in the art will appreciate the novel unique aspects of the present invention including the unique and compact configuration of the disclosed optical system and associated microprocessor controlled electronic signal processing system. In commencing the acquisition and calculation of the gas concentration signal, the electronic processing circuits are first tested to determine if the amplifier 30 should be set to a high gain stage from its normal low gain level, the high gain level for the amplifier is necessary for compensating for the aging or contamination of the components of the gas analyzer 10. This is accomplished by the application of a zero gas to the analyzer and the microprocessor executing the autogain routine of FIG. 5. During this routine the zero gas level signal derived from the infrared detector is stored in the computer memory.

With the autogain routine executed, the zero routine of FIG. 6 is executed by the microprocessor 31. During this routine the infrared source is turned off, cooled and the dark level of the analyzer is acquired and stored in the computer memory. In preparation for processing the gas data signal, the infrared beam source is turned on and the microprocessor adds a run-time offset voltage for processing the gas data signal by the analog to digital converter. To provide the correct gas data signal from the converter, the dark level signal must be substracted therefrom and the resulting value is stored for use in the gas concentration calculation per the flowchart of FIG. 7. The gas analysis process executed by the microprocessor utilizing the prior acquired signal level along with stored gas factor and polynomials for carrying the necessary calculations to obtain a digital, binary coded, output signal from the analyzer 10 to be transmitted to a host processor.

The disclosed technique for calibrating the analyzer by defining the maximum and minimum signal levels and the utilization of the D.C. or slowing changing signal level enhances the ability of the analyzer to provide an accurate gas data concentration signal with minimum noise level as the analog signals are processed and controlled by the microprocessor.

What is claimed is:

1. A method of detecting the concentration of a plurality of gases in the exhaust gases produced by the operation of a gasoline powered engine including the steps of arranging infrared light transmitting pipes for transmitting an infrared light beam over a preselected path and to exit said pipes upon transversing said path, providing an infrared light beam and projecting the beam to be transmitted over a preselected distance defined by said light transmitting pipes, mounting a first-infrared detector-filter having a narrow band infrared filter for receiving the infrared beam exiting said pipes and transmitting a preselected narrow band of the infrared beam including one of the gases to be detected to the detector and reflecting the remaining portion of the infrared beam, the step of mounting said detector-filter including mounting the detector-filter at a preselected acute angle to the path of the infrared beam exiting said pipes and receiving said exiting beam, mounting a second infrared detector-filter having a narrow band infrared filter for receiving the portion of the infrared beam reflected from said first detector-filter and transmitting a preselected narrow beam of said reflected portion of the infrared beam including a second gas to be detected to said second detector-filter and reflecting the remaining portion of said reflected portion of the infrared beam.

2. A method of detecting the concentration of a plurality of gases as defined in claim 1 wherein said second detector-filter is mounted at an angle approximately twice the angle of said first detector-filter to the axis of the path of the infrared beam exiting said pipes for receiving the portion of the infrared beam reflected from said first detector-filter.

3. A method of detecting the concentration of gases sensitive to infrared radiation including the steps of arranging a plurality of infrared transmitting pipe means in a compact arrangement including a folded optical, space savings short path along with front surface, reflective mirrors so that an infrared light beam is wholly transmitted within said pipe means except when reflected from said plane mirror surfaces for transmitting an infrared beam over a pre-selected short path with a minimum of loss of light energy and to exit said light transmitting pipe means upon traversing said folded path, said light transmitting pipe means being characterized as having smooth, reflective, internal walls for reflecting the infrared beams at said internal walls for continuously transmitting said beam longitudinally thereof, arranging a non-collimated infrared light beam source to be continuously projected through said light transmitting pipe means, mounting a first infrared detector-filter having a narrow band infrared filter for receiving the continuous infrared beam emerging from said light transmitting pipe means, said narrow band for the first detector-filter being selected to transmit a narrow band of the infrared beam representative of a first pre-selected gas to be detected and reflecting the remaining portion of said beam and thereby provide a continuous electrical output signal from said first detector-filter representative of the gas concentration of the first pre-selected gas without resorting to interrupting the beam, said reflective beam being useful for the detection of other pre-selected gases, mounting a second infrared detector-filter having a narrow band infrared filter for receiving the continuous infrared beam reflected from said first infrared detector-filter, said narrow band for the second detector-filter being selected to transmit a narrow band of the infrared beam representative of a second pre-selected gas to be detected and reflecting the remaining portion of said beam and thereby provide a continuous electrical output signal from said second detector-filter representative of the gas concentration of the second pre-selected gas, and providing means for introducing a gas mixture including the pre-selected gas to traverse said short path defined by said light pipe means and cause the infrared beam to be continuously absorbed or reduced in amplitude by an amount related to the concentration of the preselected gas whereby the electrical output signal from said detector-filter is representative of the concentration of said pre-selected gas.

4. A method of detecting the concentration of a gas sensitive to infrared radiation including the steps of arranging a plurality of infrared light transmitting pipe means in a folded, optical, space saving short path along with front surface, reflective mirrors so that an infrared light beam is wholly transmitted within said pipe means except when reflected from said plane mirror surfaces for transmitting an infrared beam over a pre-selected path and to exit said light transmitting pipe means upon traversing said folded path, said light transmitting pipe means being characterized as having smooth, reflective, internal walls for reflecting the infrared beam at said internal walls for transmitting said beam longitudinally thereof, arranging a non-collimated infrared light beam source to be projected through said light transmitting pipe means, mounting an infrared detector-filter having a narrow band infrared filter for receiving the infrared beam emerging from said light transmitting pipe means, said narrow band being selected to transmit a narrow band of the infrared beam representative of a pre-selected gas to be detected and reflecting the remaining portion of said beam and thereby provide an electrical output signal from said detector-filter representative of the gas concentration of the detected pre-selected gas, providing means for introducing a gas mixture including the pre-selected gas to traverse said path defined by said light pipe means and cause the infrared beam to be absorbed or reduced in amplitude by an amount related to the concentration of the pre-selected gas whereby the electrical output signal from said detector-filter is representative of the concentration of said pre-selected gas, and mounting another infrared detector-filter means for receiving the infrared beam reflected from said first mentioned detector-filter, said filter of said another detector-filter having a narrow band for passing a different narrow band than said first mentioned detector-filter to include a second pre-selected gas to be detected and provide an electrical output signal from said another infrared detector-filter representative of the gas concentration of the detected second pre-selected gas.

5. A method of detecting the concentration of a plurality of gases in a gas mixture including the steps of arranging infrared light transmitting pipes for transmitting an infrared light beam over a pre-selected path and to exit said pipes upon traversing said path, providing an infrared light beam and projecting the beam to be transmitted over a pre-selected distance defined by said light transmitting pipes, mounting a first-infrared detector-filter having a narrow band infrared filter for receiving the infrared beam exiting said pipes and transmitting a pre-selected narrow band of the infrared beam including one of the gases to be detected to the detector and reflecting the remaining portion of the infrared beam, the step of mounting said detector-filter including mounting the detector-filter at a pre-selected acute angle to the path of the infrared beam exiting said pipes and receiving said exiting beam, mounting a second infrared detector-filter having a narrow band infrared filter for receiving the portion of the infrared beam reflected from said first detector-filter and transmitting a pre-selected narrow beam of said reflected portion of the infrared beam including a second gas to be detected to said second detector-filter and reflecting the remaining portion of said reflected portion of the infrared beam, providing a gas input for said light transmitting pipes and a gas output port to allow the input gases or gas mixture including gases that are infrared absorbent to traverse said pre-selected path of the infrared beam between the infrared beam source and the first infrared detector-filter, providing individual electronic signal processing circuit means for receiving and processing the analog output signals from an individual one of said detector-filters for each of the detected gases, providing an analog to digital converter having a plurality of individual terminals for individually receiving each of the processed analog output signals at an input terminal from the individual signals from said signal processing signal means and providing corresponding digital output signals for each of the detected gases, providing a programmable, digital signal microprocessor having a signal storage memory for storing a program to be continuously executed and data signal storage and a plurality of signal input terminals and signal output terminals and coupled to the output signals from said analog to digital converter, introducing a gas or gas mixture that does not include any infrared absorbent gas or gases therein into said gas input port to provide "zero" gas level output signals from said detector-filters when the infrared beam source is fully on, storing said "zero" level signals in the signal memory for the microprocessor, the stored program for said microprocessor functioning to turn off the infrared beam source and permitting the source to cool for a pre-selected period prior to obtaining dark level output signals from said detector-filters, after the expiration of the pre-selected cooling period and the infrared beam source is off and cooled, acquiring the "dark" level signal and storing the dark level signal in the signal storage memory for the microprocessor, the stored program for said microprocessor then functions to turn the infrared beam source on.

introducing a gas or gas mixture that includes infrared absorbent gases into said gas input port to traverse said infrared beam path while being exposed to said beam, continuously maintaining the infrared beam source on during the presence of infrared absorbent gases for deriving analog output signals from said detector-filters that continue to be slowly reduced in amplitude for a pre-selected time period it is exposed to the infrared beam, acquiring the gas data signals representative of the concentration of the infrared absorbent gases signaled at said detector-filters, coupling the analog output signals from said detectors to said analog to digital converters for converting said input analog signals to corresponding digital, binary coded signals representative of the individual gas data signals, and causing the microprocessor to acquire said individual digital gas data signals and individual zero level signals and the individual dark level signals and causing said program to execute a gas analysis process and providing digital output signals representative of the concentration of the detected infrared absorbent gases.

6. A method of detecting the concentration of a plurality of gases as defined in claim 5 wherein said microprocessor is programmed to add an offset voltage to said gas data signals prior to coupling to said analog to digital converter only during the time intervals that infrared absorbent gases are undergoing detection for increasing the resolution of the resulting digital signals.

7. A method as defined in claim 5 or 6 wherein said electronic signal processing circuit means includes amplifying the gas data signals to a pre-selected amplitude level prior to converting the signal to a digital signal, and including storing a threshold voltage signal representative of the pre-selected amplitude level of the gas data signals in the signal storage memory for the microprocessor, causing the microprocessor to compare said stored threshold voltage signal with the signal outputs of said detectors during the time intervals a zero gas is introduced into said gas input port to determine if the compared amplified signal levels are above or below said threshold voltage signal, and if the microprocessor determination results in signal output levels below the threshold level, causing th amplifying level be increased above said pre-selected level.

8. A method as defined in claim 7 including the step of filtering out the high frequency noise from the amplified signals prior to conversion to digital signals.

9. A method as defined in claim 5 wherein the gas introduced into said gas input port comprises the exhaust gases from a gasoline powered engine.

10. A method as defined in claim 5 or 6 including repeating the steps of acquiring the zero gas signal and the dark level signals and updating the respective stored signal levels, and then repeating the step of acquiring the data signal.

* * * * *